(12) United States Patent
Hebert (10) Patent No.: US 12,131,832 B2
(45) Date of Patent: Oct. 29, 2024

(54) MICROSPHERE CONTAINMENT SYSTEMS AND METHODS

(71) Applicant: Bard Peripheral Vascular, Inc., Tempe, AZ (US)

(72) Inventor: Casey Tyler Hebert, Tempe, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 774 days.

(21) Appl. No.: 17/055,727

(22) PCT Filed: May 17, 2019

(86) PCT No.: PCT/US2019/032954
§ 371 (c)(1),
(2) Date: Nov. 16, 2020

(87) PCT Pub. No.: WO2019/222680
PCT Pub. Date: Nov. 21, 2019

(65) Prior Publication Data
US 2021/0210239 A1    Jul. 8, 2021

Related U.S. Application Data

(60) Provisional application No. 62/673,632, filed on May 18, 2018, provisional application No. 62/673,628, filed on May 18, 2018.

(51) Int. Cl.
*A61K 51/12* (2006.01)
*A61M 5/31* (2006.01)
(Continued)

(52) U.S. Cl.
CPC .......... *G21F 5/018* (2013.01); *A61K 51/1255* (2013.01); *A61M 5/3129* (2013.01);
(Continued)

(58) Field of Classification Search
CPC ......... G21F 5/015; G21F 5/018; A61K 51/00; A61K 51/12; A61K 51/1241;
(Continued)

(56) References Cited

U.S. PATENT DOCUMENTS

| 4,313,440 A | 2/1982 | Ashley |
| 5,478,323 A | 12/1995 | Westwood et al. |

(Continued)

FOREIGN PATENT DOCUMENTS

| DE | 3035290 A1 | 4/1982 |
| DE | 4318101 A1 | 12/1994 |

(Continued)

OTHER PUBLICATIONS

Chiesa, C. et al.; A dosimetric treatment planning strategy in radioembolization of hepatocarcinoma with 90Y glass microspheres; The Quarterly Journal of Nuclear Medicine and Molecular Imaging, vol. 56, No. 6; Dec. 1, 2012.

(Continued)

*Primary Examiner* — Eliza W Osenbaugh-Stewart
(74) *Attorney, Agent, or Firm* — Dinsmore & Shohl LLP (57) ABSTRACT

In the present disclosure, embodiments of microbead containment systems and containment methods are disclosed. The microbead containment system may include a microsphere container, which includes walls that define a containment space in the microsphere container, and microspheres within the containment space. The walls may include at least one magnetic component configured to produce a magnetic field within the containment space. The microspheres may include a diamagnetic material. The method of containing radioactive microspheres may include loading a plurality of microspheres comprising a diamagnetic material in a container comprising one or more magnetic components. The microspheres contained in the micro- (Continued)

sphere container interact with the magnetic field in a manner that prevents direct contact of the microspheres and the microsphere container.

17 Claims, 1 Drawing Sheet

(51) Int. Cl.
  *A61N 5/10* (2006.01)
  *G16H 20/17* (2018.01)
  *G16H 20/40* (2018.01)
  *G21F 5/018* (2006.01)
  *G21F 5/06* (2006.01)
(52) U.S. Cl.
  CPC .......... *A61N 5/1001* (2013.01); *G16H 20/17* (2018.01); *G16H 20/40* (2018.01); *G21F 5/06* (2013.01); *A61M 2205/0272* (2013.01); *A61N 2005/1019* (2013.01)
(58) Field of Classification Search
  CPC .......... A61K 51/1251; A61K 51/1255; A61M 5/1785; A61M 5/3129
  See application file for complete search history.

(56) References Cited

U.S. PATENT DOCUMENTS

| | | | |
|---|---|---|---|
| 5,496,284 A | 3/1996 | Waldenburg | |
| 6,152,913 A | 11/2000 | Feith et al. | |
| 6,159,271 A * | 12/2000 | Tillotson | B64G 1/402 96/155 |
| 6,508,807 B1 | 1/2003 | Peters | |
| 6,606,370 B1 | 8/2003 | Kasprowicz | |
| 6,723,074 B1 | 4/2004 | Halseth | |
| 7,713,239 B2 | 5/2010 | Uber, III et al. | |
| 2001/0021826 A1 | 9/2001 | Winkler | |
| 2003/0201639 A1 | 10/2003 | Korkor | |
| 2004/0111078 A1 | 6/2004 | Miyahara | |
| 2004/0258614 A1 | 12/2004 | Line et al. | |
| 2005/0085685 A1 | 4/2005 | Barbut | |
| 2006/0033334 A1 | 2/2006 | Weber et al. | |
| 2006/0091329 A1 | 5/2006 | Eguchi | |
| 2006/0293552 A1 | 12/2006 | Polsinelli et al. | |
| 2007/0129591 A1 | 6/2007 | Yanke et al. | |
| 2007/0141339 A1 | 6/2007 | Song et al. | |
| 2008/0058719 A1 | 3/2008 | Edwards et al. | |
| 2008/0103564 A1 | 5/2008 | Burkinshaw et al. | |
| 2008/0200747 A1 | 8/2008 | Wagner et al. | |
| 2009/0018498 A1 | 1/2009 | Chiu et al. | |
| 2009/0092677 A1 | 4/2009 | Richard | |
| 2009/0233586 A1 | 9/2009 | Diodati et al. | |
| 2010/0084585 A1 | 4/2010 | Prosser | |
| 2012/0190976 A1 | 7/2012 | Kleinstreuer | |
| 2012/0201726 A1 | 8/2012 | Pearcy et al. | |
| 2012/0289780 A1 * | 11/2012 | Farkas | A61B 5/6861 604/93.01 |
| 2013/0049187 A1 | 2/2013 | Minamio | |
| 2013/0165899 A1 | 6/2013 | Haueter et al. | |
| 2013/0317277 A1 | 11/2013 | Lemer | |
| 2014/0046295 A1 | 2/2014 | Uber, III et al. | |
| 2014/0163302 A1 | 6/2014 | Fox et al. | |
| 2014/0207178 A1 | 7/2014 | Chomas et al. | |
| 2014/0236093 A1 | 8/2014 | Eggert et al. | |
| 2014/0257233 A1 | 9/2014 | Cowan | |
| 2015/0273089 A1 | 10/2015 | Gray | |
| 2015/0285282 A1 | 10/2015 | Weitz et al. | |
| 2016/0325047 A1 | 11/2016 | Vedrine et al. | |
| 2016/0331853 A1 | 11/2016 | Taub | |
| 2016/0331998 A1 | 11/2016 | Hoffman et al. | |
| 2017/0065732 A1 | 3/2017 | Srinivas et al. | |
| 2017/0120032 A1 | 5/2017 | Miyazaki et al. | |
| 2017/0151357 A1 | 6/2017 | Cade | |
| 2017/0189569 A1 | 7/2017 | Souresrafil et al. | |
| 2017/0238951 A1 | 8/2017 | Yang et al. | |
| 2017/0304151 A1 | 10/2017 | Van Den Berg et al. | |
| 2018/0185040 A1 | 7/2018 | Seip | |
| 2018/0214707 A1 * | 8/2018 | Li | A61K 41/0052 |
| 2019/0338807 A1 * | 11/2019 | Willmot | B64G 1/50 |

FOREIGN PATENT DOCUMENTS

| | | |
|---|---|---|
| EP | 2179758 A2 | 4/2010 |
| FR | 2917981 A1 | 1/2009 |
| JP | 2006017660 A | 1/2006 |
| JP | 2010068603 A | 3/2010 |
| JP | 2013071082 A | 4/2013 |
| WO | 2007008511 A2 | 1/2007 |
| WO | 2009039203 A2 | 3/2009 |
| WO | 2011014562 A1 | 2/2011 |
| WO | 2012006555 A1 | 1/2012 |
| WO | 2012118687 A1 | 9/2012 |
| WO | 2013153722 A1 | 10/2013 |
| WO | 2014165058 A1 | 10/2014 |
| WO | 2016049685 A1 | 4/2016 |
| WO | 2016161346 A1 | 10/2016 |
| WO | 2017053398 A1 | 3/2017 |
| WO | 2017157974 A1 | 9/2017 |
| WO | 2019006099 A1 | 1/2019 |
| WO | 2019222699 A1 | 1/2019 |
| WO | 2019222687 A1 | 11/2019 |
| WO | 2019222700 A1 | 11/2019 |
| WO | 2019222713 A1 | 11/2019 |

OTHER PUBLICATIONS

Chiesa, C. et al.; Radioembolization of hepatocarcinoma with 90Y glass microspheres: development of an individualized treatment planning strategy based on dosimetry and radiobiology; European Journal of Nuclear Medicine and Molecular Imaging, Springer Verlag, Heidelberg, DE; vol. 42; No. 11; Jun. 27, 2015.
Spreafico, C. et al.; The dosimetric importance of the number of 90Y microspheres in liver transarterial radioembolizaiton (TARE); European Journal of Nuclear Medicine and Molecular Imaging, Springer Verlag, Heidelberg, DE; vol. 41, No. 4; Jan. 30, 2014.
International Search Report and Written Opinion dated Aug. 1, 2019 pertaining to International Application No. PCT/US2019/032983.
International Search Report and Written Opinion dated Dec. 13, 2019 pertaining to International Application No. PCT/US2019/032987.
International Search Report and Written Opinion dated Oct. 16, 2019 pertaining to International Application No. PCT/US2019/032955.
International Search Report and Written Opinion dated Jul. 23, 2019 pertaining to International Application No. PCT/US2019/032950.
International Search Report and Written Opinion dated Sep. 24, 2019 pertaining to International Application No. PCT/US2019/033011.
International Search Report and Written Opinion dated Jul. 26, 2019 pertaining to International Application No. PCT/US2019/032965.
International Search Report and Written Opinion dated Jul. 29, 2019 pertaining to International Application No. PCT/US2019/032954.
International Search Report and Written Opinion dated Aug. 7, 2019 pertaining to International Application No. PCT/US2019/032986.
Arepally, A.; Quantification and Reduction of Reflux during Embolotherapy Using an Antireflux Catheter and Tantalum Microspheres: Ex Vivo Analysis; J Vasc Interv Radiol; 2013; 24:575-580.
Chung, J. et al.; Novel use of the Surefire antireflux device in subtotal splenic embolization; Journal of Vascular Surgery Cases; Dec. 1, 2015; pp. 242-245; vol. 1, No. 4.
Ho, S. et al; Clinical evaluation of the partition model for estimating radiation doses from yttrium-90 microspheres in the treatment of hepatic cancer; European Journal of Nuclear Medicine, Springer, Berlin, Heidelberg, DE: vol. 24. No. 3; Mar. 1, 1997.
Hospital Clinics et al.; Y-90 MicroSpheres (SIRSpheres) for treatment of hepatocellular carcinoma; Mar. 1, 2017.

(56) References Cited

OTHER PUBLICATIONS

Morshedi, M. et al.; Yttrium-90 Resin Microsphere Radioembolization Using an Antireflux Catheter: An Alternative to Traditional Coil Embolization for Nontarget Protection; Cardiovasc Intervent Radiol; 2015; 38:381-38; Springer.
Sirtex Medical Limited: Sirtex Medical Products Pty Ltd SIR-Spheres (Ytttrium-90 Microspheres); Apr. 1, 2005.
Theragenics Corp.; Therasphere IDOC TM; Aug. 4, 2015.
Tong, A. et al; Yttrium-90 hepatic radioembolization: clinical review and current techniques in interventional radiology and personalized dosimetry; British Journal of Radiology; vol. 89, No. 1062; Jun. 1, 2016.
US FDA; Theresphere IDOC—Humanitarian Device Exemption (HDE); Sep. 14, 2015.
Westcott, M. et al.; The development, commercialization, and clinical context of yttrium-90 radiolabeled resin and glass microspheres; Advances in Radiation Oncology; 2016; vol. 1; pp. 351-364.
Sirtex Medical Limited; SMAC-SIR-Spheres Microspheres Activity Calculator; May 6, 2018.
Office Action dated Feb. 17, 2023 pertaining to JP Patent Application 2020-564535.
NZ Examination Report dated Nov. 9, 2024 pertaining to NZ application No. 770700.
Australian Examination Report dated Mar. 26, 2024 pertaining to AU application No. 2019270182 filed Dec. 3, 2020.

\* cited by examiner

MICROSPHERE CONTAINMENT SYSTEMS AND METHODS

CROSS-REFERENCE TO RELATED APPLICATIONS

This application is a National Stage Entry under 35 U.S.C. § 371 of International Patent Application No. PCT/US2019/032954, entitled "MICROSPHERE CONTAINMENT SYSTEMS AND METHODS", filed May 17, 2019, which claims the benefit of priority to U.S. Provisional App. No. 62/673,632, entitled "RADIOEMBOLIZATION DELIVERY DEVICE" filed May 18, 2018, the disclosure of which is incorporated by reference herein; and to U.S. Provisional App. No. 62/673,628, entitled "DUAL-STAGE SYRINGES WITH LOCKING MECHANISM" filed May 18, 2018, the disclosure of which is incorporated by reference herein.

TECHNICAL FIELD

The present disclosure relates generally to containment systems for radioactive or volatile substances and, more particularly, to containment systems for particles that include radioactive or volatile substances.

BACKGROUND

In radiation physics, the amount of radiation deposited in a certain amount (mass) of tissue or other solid object is referred to as an absorbed dose. The unit for absorbed dose is the gray (Gy). Absorbed dose is proportional to the inverse square of the distance (R) from the tissue to the radioactive source, such as a radioactive microbead (i.e. dose=$1/R^2$). For example, for every doubling of distance from the radioactive source, the absorbed dose decreases to one fourth the amount from the original distance.

Microspheres utilized for radioembolization medical treatment may emit a dose of radiation to materials and tissues surrounding the microbead materials. When such microspheres are in a stored container such as a glass vial, the microspheres can settle out of solution and directly contact the container (i.e., R=0). If the radioactive microspheres remain in that position for an extended period of time (for example, greater than 1 week), the container may experience an absorbed dose of approximately 5,000 kGy, which is equivalent to approximately 150 gamma sterilization cycles. Depending on the material of container, the absorbed dose may cause the container to become brittle, cracked, flaked, discolored, or otherwise integrity compromised.

SUMMARY

Microspheres utilized for radioembolization treatments may conventionally be stored in containers, such as glass vials, for weeks at a time. Therefore, such containers used to store radioactive microspheres for radioembolization may absorb greater than 5,000 kGy of radiation dose. Despite browning and embrittlement under such circumstances, glass vials remain an industry standard for storage of radioactive materials. However, the manufacture of glass containers is more costly than the manufacture of plastic containers.

Another challenge of storing and administering radioembolization microspheres concerns the potential for the microspheres to cling to the container or to delivery lines as a result of static electricity, lubricants used, the microspheres' geometry, or the container's geometry. In the case of radioembolization microspheres, residual microspheres that cling to the vials and delivery lines pose a risk to physicians. Moreover, the residual microspheres may result in misadministration.

Therefore, ongoing needs exist for containment systems for the storage of microspheres used for radioembolization, which include materials that may reduce interaction or binding of the microspheres with the container and browning or embrittlement of the container.

The proposed containment systems meet the foregoing needs by incorporating the principles of diamagnetism. Most nonferrous materials, such as graphite and bismuth, naturally repel from magnetic poles. By adjusting the power of the magnetic field, a plurality of microspheres that include diamagnetic materials may be repelled or "levitated" at a certain distance from one or more magnetic surfaces of a container.

Accordingly, example embodiments disclosed herein are directed to containment systems for use in medical settings where microspheres or particles containing hazardous or volatile substances are stored and subsequently administered, such as radioembolization microspheres. The presently disclosed containment systems may reduce interaction or binding of such microspheres with the containers when compared to conventional containers, such as syringes and vials, currently used in radioembolization treatment. Additionally, in some embodiments, non-uniform magnetic fields along the vessel may facilitate the mixing of the microspheres in the suspension medium.

According to at least one embodiment of the present disclosure, a microbead containment system is provided. A microsphere containment system for storing microspheres including a diamagnetic material may include a microsphere container comprising walls that define a containment space in the microsphere container, the walls comprising at least one magnetic component configured to produce a magnetic field within the containment space. The microspheres including a diamagnetic material, when stored within the containment space, may interact with the magnetic field within the containment space in a manner that prevents direct contact between of the microspheres and with the walls of the microsphere container.

According to at least one embodiment of the present disclosure, a microbead containment method is provided. The method may include loading microspheres comprising a diamagnetic material into a microsphere container comprising walls that define a containment space in the microsphere container. The walls may include at least one magnetic component configured to produce a magnetic field within the containment space. The microspheres in the microsphere container may interact with the magnetic field in a manner that prevents direct contact of the microspheres to the container.

These and other features, aspects, and advantages of the present disclosure will become better understood with reference to the following description and the appended claims.

Additional features and advantages of the embodiments described herein will be set forth in the detailed description that follows, and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an over-view or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Specific embodiments of the present application will now be described. These embodiments are provided so that this disclosure will be thorough and complete and will fully convey the scope of the subject matter to those skilled in the art.

Reference will now be made in detail to embodiments of microbead containment systems. The microbead containment systems described herein may include a plurality of microspheres comprising a diamagnetic material and a container comprising one or more magnetic walls. In embodiments, the walls of the container may include one or more magnetic components, which may influence the distribution or behavior of the plurality of microspheres within the container. As subsequently described in more detail, the one or more magnetic walls may produce a magnetic field that repels the diamagnetic material of the plurality of microspheres. This repulsion between the magnetic walls and the diamagnetic material of the beads may cause the plurality of microspheres to levitate within the container.

Figure 1:
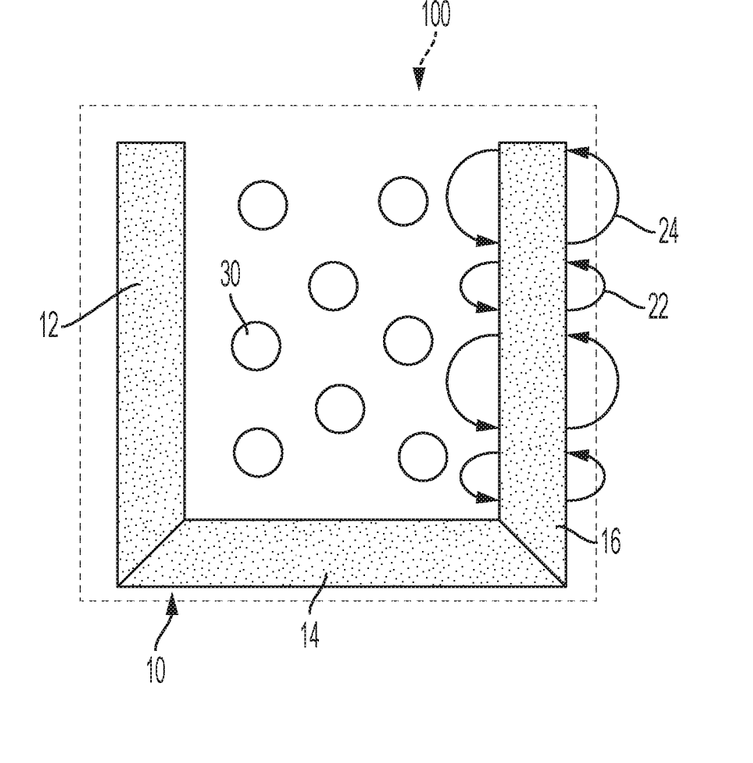
FIG. 1 is an illustration of a microbead containment system according to embodiments.

Referring now to FIG. 1, a section view of an embodiment of a microbead containment system 100 is provided. In FIG. 1, the microbead containment system 100 may include a container 10, formed by walls 12, 14, 16. The container 10 may contain a plurality of microspheres 30. Additionally, the walls 12, 14, 16 of the container 10 may produce one or more magnetic fields of varying sizes, illustrated as greater magnetic fields 24 and lesser magnetic fields 22.

Reference will now be made in detail to embodiments of the container 10. The container 10 may be any barrel, vessel, box, vial, receptacle, or tank that defines a containment space and is suitable for storing the plurality of microspheres 30 previously described herein. In some specific embodiments, the container 10 may be a syringe barrel. In the exemplary embodiment depicted in the section view of FIG. 1, the container 10 may be a box with a base wall and four side walls. In the section view shown in FIG. 1, the container 10 includes a base wall 14 and side walls 12 and 16. The container may also include front walls and back walls not shown in FIG. 1. In other embodiments, the container may include walls of any shape, including walls that are rounded, cylindrical, or angled, for example, provided the walls form a container suitable for containing the plurality of microspheres 30. In some embodiments, the container may include a lid, a top wall, septum or other solid feature that seals the plurality of microspheres within the container 10.

The container 10 may be made from any suitable gamma compatible material. A gamma compatible material may be any radiation-stable, medical-grade polymer material, such as those provided subsequently in Table 1.

TABLE 1

| Gamma Compatible Materials | |
|---|---|
| MATERIAL | TOLERANCE LEVEL (KGY) |
| Thermoplastics | |
| Acrylonitrile/Butadiene/Styrene (ABS) | 1,000 |
| Aromatic Polyesters (PET, PETG) | 1,000 |
| Cellulosics | |
|    Esters and Ethers | 100 |
|    Paper, Card, Corrugated, Fibers | 100-200 |
|    Cellulose Acetate Propiconate and Butyrate | 100 |
| Fluoropolymers | |
|    Tetrafluroethylene (PTFE) | 5 |
|    Polychlorotrifluoroethylene (ECTFE) | 200 |
|    Polyvinyl Fluoride | 1,000 |
|    Polyvinylidene Fluoride (PVDF) | 1,000 |
|    Ethylene-Tetrafluoroethylene (ETFE) | 1,000 |
|    Fluorinated Ethylene Propylene (FEP) | 50 |
| Polyacetals (Delrin, Celcon) | 5 |
| Polyacrylics | |
|    Polymethylmethacrylate | 100 |
|    Polyacrylonitrile | 100 |
|    Polyacrylate | 100 |
|    Polycyanoacrylate | 200 |
| Polyamides (Nylons) | |
|    Aliphatic & Amorphous Grades | 50 |
|    Aromatic Polyamide/Polyimide | 10,000 |
| Polycarbonate | 1,000 |
| Polyethylene (LDPE, LLDPE, HDPE, UHMPE, UHMWPE) | 1,000 |
| Polyimides | 10,000 |
| Polymethylpentene | 20 |
| Polyphenylene Sulfide | 1,000 |

TABLE 1-continued

Gamma Compatible Materials

| MATERIAL | TOLERANCE LEVEL (KGY) |
|---|---|
| Polypropylene, Radiation Stabilized | 20-50 |
|    Homopolymer | 20-50 |
|      Copolymers of Propylene-Ethylene | 25-60 |
|      Polypropylene, natural | 20 |
| Polystyrene | 10,000 |
| Polysulfone | 10,000 |
| Polyurethane | 10,000 |
| Polyvinylbutyral | 100 |
| Polyvinylchloride (PVC) | 100 |
| Polyvinylidene Chloride (PVDC) | 100 |
| Styrene/Acrylonitrile (SAN) | 1,000 |
| Thermosets | |
| Allyl Digylcol Carbonate (Polyester) | 5,000-10,000 |
| Epoxies | 1,000 |
| Phenolics | 50,000 |
| Polyesters | 100,000 |
| Polyurethanes | 100-1,000 |
| Elastomers | |
| Butyl | 50 |
| Ethylene-Propylene Diene Monomer (EPDM) | 100-200 |
| Fluoro Elastomer | 50 |
| Natural Rubber (Isoprene) | 100 |
| Nitrile | 200 |
| Polyacrylic | 50-200 |
| Polychloroprene (Neoprene) | 200 |
| Silicones (Peroxide & Platinum Catalyst systems) | 50-100 |
| Styrene-Butadiene | 100 |
| Urethanes | 100-200 |

The radiation stability of the gamma compatible material may be dependent on the tolerance level of the particular type of medical grade polymer material. Once the container material absorbs a radiation dose that exceeds the container material's tolerance level, browning or embrittlement of the container 10 may occur. Exemplary gamma compatible materials include, but are not limited to, thermoplastics, including acrylonitrile/butadiene/styrene, aromatic polyesters, cellulosics, fluoropolymers, polyacetals, polyacrylics, polyamides, polyethylenes polyimides, polymethylpentene, polyphenylene sulfide, polypropylenes, polystyrenes, polysulfones, polyurethanes, polyvinylbutyral, polyvinylchloride, polyvinylidene chloride, styrene/acrylonitrile; thermosets including allyl digylcol carbonate, epoxies, phenolics, polyesters, polyurethanes, and elastomers including butyl, ethylene-propylene diene monomer, fluoro elastomers, natural rubbers, nitriles, polyacrylics, polychloroprenes, silicones, styrene-butadienes, and urethanes. The radiation tolerance of the elastomers may be affected by the base polymer and the curing system used. In some embodiments, the container 10 may be made from a gamma compatible material with a tolerance level of from about 5 kGy to about 100,000 kGy, from about 5 kGy to about 10,000 kGy, from about 5 kGy to about 5,000 kGy, from about 5 kGy to about 1,000 kGy, from about 5 kGy to about 500 kGy, from about 5 kGy to about 100 kGy, from about 100 kGy to about 100,000 kGy, from about 100 kGy to about 10,000 kGy, from about 100 kGy to about 5,000 kGy, from about 100 kGy to about 1,000 kGy, from about 100 kGy to about 500 kGy, from about 500 kGy to about 100,000 kGy, from about 500 kGy to about 10,000 kGy, from about 500 kGy to about 5,000 kGy, from about 500 kGy to about 1,000 kGy, from about 1,000 kGy to about 100,000 kGy, from about 1,000 kGy to about 10,000 kGy, from about 1,000 kGy to about 5,000 kGy, from about 5,000 kGy to about 100,000 kGy, from about 5,000 kGy to about 10,000 kGy, or from about 10,000 kGy to about 100,000 kGy.

In embodiments, the walls of the container 10 may include one or more magnetic fields. The one or more magnetic fields of the container 10 may interact with the plurality of microspheres 30 in a manner that prevents direct contact of the plurality of microspheres to the container. In some embodiments, the one or more magnetic fields of the container 10 may interact with the plurality of microspheres 30 in a manner that facilitates mixing of the plurality of microbeads. The mixing may, at least in part, be facilitated by the shape of the walls of the container 10. In embodiments, the strength, location, and pattern of the one or more magnetic fields of the container 10 may vary. The magnetic fields may be of sufficient magnitude to levitate or repel the plurality of microspheres 30 off the surface of the container 10. This magnitude may be depend on various factors, including the radiation tolerance of the container material; the amount of therapeutic agent in the microsphere, more specifically, the amount of radiotherapeutic material in the microsphere; the type of therapeutic agent in the microsphere, more specifically, the amount of radiotherapeutic material in the microsphere; the amount (mass) of microsphere material, the type of microsphere material, the amount (mass) of diamagnetic material, the type of diamagnetic material, and combinations of these factors. The magnetic fields may be of sufficient magnitude to levitate or repel the plurality of microspheres at a height sufficient to prevent browning or embrittlement of the container 10. Without being bound by theory, because the dose is reduced by $1/R^2$, relatively small changes in distance can have a substantial impact on the dose absorbed by the container 10.

In some embodiments, the container 10 may include multiple magnetic fields. In further embodiments, the container 10 may include multiple magnetic fields of varying strengths (e.g. multiple zones having varying magnitudes of magnetic field strength). For example, at least a portion of the magnetic fields of the container 10 may be of a lesser strength 24, and at least a portion of the magnetic fields of the container 10 may be of a greater strength 24. The varying strengths of the magnetic fields of the container 10 may facilitate mixing of the plurality of microspheres 30 within the container 10.

In embodiments, the magnetic fields of the container 10 may be produced by incorporating one or more magnetic components into the walls of the container 10. In other embodiments, the magnetic fields of the container 10 may be produced by surrounding the container 10 with one or more magnetic components. When the walls of the containers described herein comprise one or more magnetic components, the walls may comprise any number of individual magnetic components (e.g., one, two, three, four, five, six, seven, or eight or more, etc.). Each magnetic component may be fixed in or on the container 10 by any suitable method. For example, in some variations one or more magnetic components may be embedded in, adhered to, or friction-fit within the container 10 by any suitable manufacturing methods, including by painting, over-molding, printing, or gluing the one or more magnetic components onto the container 10. In embodiments where one or more magnetic components surround the container 10, each magnetic component may not be fixed in or on the container 10, so the magnetic fields produced by the magnetic components may be mobile. In further embodiments where one or more magnetic components surround the container 10, each magnetic component may be embedded in, adhered to, or friction-fit within a casing, cover, or other external component that surrounds at least a portion of the container 10.

In embodiments, the magnetic component may include a permanent magnet. The magnet may be made of any suitable material capable of generating a magnetic field. In some embodiments, the magnetic components may be permanent magnets made out of ferromagnetic materials. For example, in some variations, the magnetic components may comprise one or more rare-earth magnets, cobalt, gadolinium, iron, nickel, alloys of these metals with or without other metals such as alnico, chemical compounds such as ferrites, or a combination of any of these metals or their alloys. In further embodiments, the rare-earth magnets may include samarium cobalt magnets or neodymium magnets.

In embodiments, the magnetic component may include an electromagnet. When a magnetic component comprises an electromagnet, the electromagnet may be selectively activated to produce a magnetic field. For example, when one or more container walls of the systems described here comprise one or more electromagnets, the electromagnets may be activated before the plurality of microspheres 30 are loaded in the container; the electromagnets may remain activated during storage of the plurality of microspheres 30 to levitate the plurality of microspheres 30 and keep them from settling in the container 10; and then the electromagnets may be deactivated after the plurality of microspheres 30 are removed from the container or after the radioembolization procedure is complete. When the container comprises multiple electromagnets, these magnetic components may be independently activated or may be activated as a group. In embodiments, the one or more electromagnets may be selectively activated by an electronic interaction, such as by a battery and a switch or other suitable activating means. In some embodiments, the one or more electromagnets may be selectively activated in a manner to create one or more pulsating magnetic fields. In further embodiments, multiple electromagnets may be selectively activated in a manner to create multiple pulsating magnetic fields with varying magnitudes.

In embodiments, the container may include multiple magnetic components. In further embodiments, the multiple magnetic components may be any combination of permanent magnets, ferromagnetic components, or electromagnets. In one exemplary embodiment, only the side walls (i.e., the side wall 12, the side wall 16, the front wall not shown in FIG. 1, and the back wall not shown in FIG. 1) of the container 10 may include permanent magnets. In these variations, the base wall 14 may include only permanent magnets, only ferromagnetic components, only electromagnets, or a mix of some or all of these elements. In the side walls of the container 10 may include permanent magnets, and the base wall 14 or a lid may include only electromagnets that may be activated after the plurality of microspheres 30 have been loaded into the container 10.

In embodiments, each magnetic component may have any suitable size and shape. For example, each magnetic component may be cylindrical, semi-cylindrical, tube-shaped, box-shaped, planar, spherical, or the like. Generally, the dimensions of the magnetic components may be constrained by size of the containers carrying the magnetic components, which in turn may be constrained by the radioembolization procedure itself. For example, the radioembolization procedure may require a specific dose or delivery device, in which case, the container 10 may be specifically sized to accommodate said dose or fit within said delivery device. Each magnetic component may have any suitable length. In some embodiments, each magnetic component may have a length of about 5 mm, about 10 mm, about 15 mm, about 20 mm, or each magnetic component may extend along the entire length of one wall of the container 10.

Reference will now be made in detail to embodiments of the plurality of microspheres 30. The plurality of microspheres 30 may include multiple microspheres, which may be regularly or irregularly shaped, which may also be referred to as a "microbeads." In some embodiments, the plurality of microspheres may alternatively include a plurality of particles, which may be regularly or irregularly shaped, or a plurality of flakes, which may be regularly or irregularly shaped. In other embodiments, the plurality of microspheres 30 may include a combination of microspheres, particles, and/or flakes. In other embodiments, the plurality of microspheres 30 may include one or more composite particle that includes a conglomerate of microspheres, particles, flakes, or combinations. In embodiments, the plurality of microspheres 30 may include any microspheres suitable for use in embolization treatment procedures, such as microspheres used as scout beads or microspheres used for therapeutic treatment. In embodiments of the microbead containment system 100 described herein, the plurality of microspheres 30 includes microspheres that comprise a diamagnetic material or a therapeutic agent. In further embodiments, the plurality of microspheres 30 includes microspheres that comprise a diamagnetic material and a therapeutic agent. In further embodiments, the plurality of microspheres 30 includes microspheres that comprise a diamagnetic material and a therapeutic agent and a microbead material. In some embodiments, each microbead in the plurality of microspheres 30 may include the diamagnetic material, the therapeutic agent, and the microbead material. In some embodiments, only some of the microspheres in the plurality of microspheres 30 may include the diamagnetic material, the therapeutic agent, or a combination of the diamagnetic material and the therapeutic agent.

Individual microspheres of the plurality of microspheres 30 may have diameters of a size suitable radioembolization medical treatment. In some embodiments, individual microspheres of the plurality of microspheres 30 may have diameters of about 30 micrometers (μm) to about 1500 μm. In other embodiments, the individual microspheres of the plurality of microspheres 30 may have diameters of about 30 μm to about 1500 μm, about 30 μm to about 1000 μm, about 30 μm to about 500 μm, about 30 μm to about 100 μm, about 100 μm to about 1500 μm, about 100 μm to about 1000 μm, about 100 μm to about 500 μm, about 500 μm to about 1500 μm, about 500 μm to about 1000 μm, or about 1000 μm to about 1500 μm.

The microspheres of the plurality of microspheres 30 may include a microbead material. In some embodiments, the microbead material may include glass or silica. In other embodiments, the microbead material may include biodegradable and bioresorbable materials, which are materials that degrade and/or are reabsorbed safely within the body. Examples of biodegradable and bioresorbable materials may include, without limitation, polyglycolic acid (PGA), polyhydroxy butyrate (PHB), polyhydroxy butyrates-co-beta hydroxyl valerate (PHBV), polycaprolactone (PCL), Nylon-2-nylon-6, polylactic-polyglycolic acid copolymers, PLGA-polyethylene glycol (PEG)-PLGA (PLGA-PEG-PLGA), carboxymethylcellulose-chitosan (CMC-CCN), chitosan, hydroxyethyl acrylate (HEA), iron-based alloys, magnesium-based alloys, and combinations thereof. In other embodiments, the microbead material may be a polymer material. In further embodiments, the microbead material may be a water-swellable polymer material, such as a polymer material capable of forming a hydrogel. The microspheres of the plurality of microspheres 30 may have any shape common to microparticles formed from microbead material, or more specifically, a hydrogel type water-swellable polymer material. For example, the microspheres of the plurality of microspheres 30 may be spherical or substantially spherical, may have an ovoid shape with oval-shaped or elliptical cross-sections about a longitudinal axis and circular cross-sections about an axis perpendicular to the longitudinal axis, or combinations thereof. In some embodiments, the microspheres may be porous.

In various embodiments, the microbead material may include water-swellable polymer material that includes a natural hydrogel polymer such as a chitosan or a polysaccharide, or a synthetic hydrogel polymer such as a polyacrylate, a polyamide, a polyester, a polysaccharide, a poly(methylmethacrylate), or a poly(vinyl alcohol), for example. In some embodiments, the water-swellable polymer material may be biodegradable. Specific examples of water-swellable polymer materials include, without limitation, poly(4-hydroxybutyrate), methacrylated hyaluronic acids (hyaluronic acids being polymers of disaccharides composed of D-glucuronic acid and N-acetyl-D-glucosamine), chitosan-alginates, poly(N-isopropylacrylamide) copolymers, poly(N-isopropylacrylamide)-alginates, poly(N-isopropylacrylamide)-peptides, poly(N-isopropylacrylamide)-α-acryloyloxy-β,β-dimethyl-γ-butyrolactone-hydrophilic Jeffamine, or poly(N-isopropylacrylamide)-poly(ethylene glycol) diacrylate-pentaerythritol tetrakis(3-mercapto-propionate). The microbead material may include may include water-swellable polymer materials that include derivatives of any of the foregoing materials, or may include combinations of any of the foregoing materials or their derivatives. For example, the microbead material may include a combination of multiple water-swellable polymer materials, in which each individual microbead is made of a single type of polymer, and the plurality of microspheres 30 includes microbead materials of multiple polymer types. In some embodiments, the microbead material may include a combination of multiple water-swellable polymer materials, in which individual microspheres are composed of multiple types of polymer.

In embodiments, the individual microspheres of the plurality of microspheres 30 may include from about 30% by weight to about 70% by weight, or from about 35% by weight to about 65% by weight, or from about 40% to about 60% by weight, or about 45% by weight to about 55% by weight, or about 50% to about 70% by weight microbead material, based on the total weight of the individual microspheres. In further embodiments, individual microspheres of the plurality of microspheres 30 may include from about 30% by weight to about 70% by weight, or from about 35% by weight to about 65% by weight, or from about 40% to about 60% by weight, or about 45% by weight to about 55% by weight, or about 50% to about 70% by weight water-swellable polymer material, based on the total weight of the individual microspheres in the plurality of microspheres 30.

As stated previously, the plurality of microspheres 30 may include one or more diamagnetic materials. In particular, a diamagnetic material is a material that is repelled by both poles of a dipole magnet. When a diamagnetic material is placed within an external magnetic field, the magnetic fields created by the electrons of diamagnetic material point in a direction opposite that of the external magnetic field. Because opposing magnetic fields naturally repel each other, this interaction results in a repulsive force.

Therefore, in embodiments, the plurality of microspheres 30 may include one or more diamagnetic materials, which may exhibit magnetic repulsion to the external magnetic field produced by the magnetic container walls 12, 14, 16, thereby allowing the plurality of microspheres 30 to move according to the magnetic repulsion. In some embodiments, the one or more diamagnetic materials of the plurality of microspheres 30 may exhibit electromagnetic repulsion to an applied electrical current, an electrical field, or both, which thereby allows the plurality of microspheres 30 to move according to the electromagnetic repulsion. In a non-limiting example, the plurality of microspheres 30 may move away from the container 10 when the plurality of microspheres 30 comprise one or more diamagnetic materials that are magnetically or electromagnetically repelled from the container walls 12, 14, and 16.

Illustrative materials that react to an electrical current or electrical field may include, but are not limited to, metals, electrolytes, superconductors, semiconductors, nonmetallic conductors, conductive polymers, shape memory polymers, and shape memory alloys. In embodiments, illustrative diamagnetic materials may include, but are not limited to, water, wood; glass; ceramics; carbon, graphite; organic compounds such as petroleum, plastic, biological tissue; and metals such as copper, mercury, gold, and bismuth. In some embodiments, the one or more microspheres may include one or more of glass, ceramics, carbon, graphite, metals, or combinations thereof. In some specific embodiments, the one or more microspheres may include one or more of graphite, bismuth, or combinations thereof, which may be selected for economical benefits during the manufacturing process or for performance benefits.

In the microspheres of the plurality of microspheres 30, the one or more diamagnetic materials may be generally surrounded by the microbead material. In some embodiments, the water-swellable polymer material or some portion thereof may generally surround the one or more diamagnetic materials. In other embodiments, a microbead material shell, such as a water-soluble polymer material shell, may encapsulate a core that holds the one or more diamagnetic materials. In other embodiments, the one or more diamagnetic materials may be physically disposed within a matrix, network, or pore structure of the microbead material that may or may not have a core within an outer shell. In other embodiments, the one or more diamagnetic materials may be coated onto or otherwise chemically-bonded to the microbead material, such that the one or more diamagnetic materials have covalent chemical bonds with the microbead material.

In embodiments, the one or more diamagnetic materials may lack covalent chemical bonds with the microbead material but may in some instances interact noncovalently, ionically, or through van der Waals forces with the microbead material. For example, if the microbead material is a polymer material, the one or more diamagnetic materials may lack covalent bounds with the polymer material entirely or the microbead material may lack covalent bonds with just the polymer backbone of the polymer material. In further embodiments, the one or more diamagnetic materials may lack covalent bonds with the water-swellable polymer material entirely or the microbead material may lack covalent bonds with just the polymer backbone of the water-swellable polymer material. In further embodiments, the microbead material may generally surround the one or more diamagnetic materials, yet the one or more diamagnetic materials may be covalently bonded to a functional group of the water-swellable polymer material.

In some embodiments, one or more diamagnetic materials may be incorporated into the microspheres to produce a loaded resin material. A loaded resin material may refer to a microbead material that includes the one or more diamagnetic materials physically disposed within a matrix, network, or pore structure throughout the microsphere material. In some specific embodiments, the loaded resin material may be a graphite-loaded material or a bismuth-loaded material.

In embodiments of incorporating the one or more diamagnetic materials into the microspheres, the microspheres may have a core-shell morphology, where the shell includes the microbead material, and the core, encapsulated by the shell, includes the one or more diamagnetic materials or the loaded resin material. The term "encapsulated" broadly includes embodiments for which the shell or some portion thereof generally surrounds the core. In some specific embodiments, where the microspheres have a core-shell morphology, the shell includes polycarbonate or nylon, and the core includes the loaded resin material. In other embodiments, the one or more diamagnetic materials or the loaded resin material may be the core material encapsulated in a biocompatible resin shell. Examples of the biocompatible resin may include, without limitation, epoxy resins, polyether ether ketone resins, high-density polyethylenes, or combinations thereof. In some embodiments, the biocompatible resin material may be used to separate the one or more diamagnetic materials or the loaded resin material from one or more other functional layers in the microbead. The microspheres having a core-shell morphology may be produced by a microfluidic manufacturing process. In other embodiments, the loaded resin material may be physically disposed within a matrix, network, or pore structure of the microbead material that may or may not have a core within an outer shell.

As stated previously, the diamagnetic material may allow the plurality of microspheres 30 to remain suspended for delivery. The diamagnetic material may reduce interaction or binding of the microspheres with the container 10. For example, the diamagnetic material may allow the container 10, described subsequently in more detail, to resist browning or embrittlement from radiation exposure.

Conventional containers used for storing microspheres for embolization may include, for example, glass vials. During storage, the microspheres, which may include radiotherapeutic agents but do not contain a diamagnetic material, can settle out in the conventional containers, thereby coming into direct contact with the conventional container. Over time, as the microspheres for embolization remain in that position within the conventional containers for an extended period of time (for example, greater than one week), the glass of a conventional container may absorb upwards of approximately 5,000 kGy of radiation dose. Consequently, this extended radiation dose may cause the materials of conventional containers to become brittle, crack, flake, discolor, or otherwise integrity compromised.

In contrast, in the presently-disclosed containment systems 100, when an external magnetic field is applied to the container 10, microspheres that contain the diamagnetic material are repelled away from the external field. In particular, the plurality of microspheres 30 are repelled from the walls 12, 14, 16 of the container 10. Resultantly, the plurality of microspheres 30 do not settle out in the container 10 or come into direct contact with the container 10. Rather, the plurality of microspheres 30 may remain suspended within the container 10 without clinging to the container 10. Additionally, because the plurality of microspheres 30 do not settle out in the container 10 or come into direct contact with the container 10, the container 10 absorbs a radiation dose less than the dose that would result when the microspheres do contact the container.

Without being bound by theory, the amount of diamagnetic material incorporated into the microspheres, thereby allowing them to be repelled from the container 10, may depend on various factors, including the weight of the individual microsphere and the distance the microsphere needs to be repelled from the container 10. In example embodiments, the individual microspheres of the plurality of microspheres 30 may include from about 1% by weight to about 25% by weight, or from about 1% by weight to about 20% by weight, or from about 1% by weight to about 15% by weight, or from about 2% by weight to about 25% by weight, or from about 5% by weight to about 25% by weight, or from about 10% by weight to about 25% by weight diamagnetic material, based on the total weight of the individual microspheres in the plurality of microspheres 30.

In embodiments, the plurality of microspheres 30 may include one or more drug-loaded microspheres. In some embodiments, the plurality of microspheres 30 may be entirely made up of drug-loaded microspheres, where each microbead also includes a diamagnetic material. In other embodiments, the plurality of microspheres 30 may include a mixture of drug-loaded microspheres and microspheres that include a diamagnetic material.

In embodiments, the drug-loaded microspheres may be microspheres loaded with a therapeutic agent or with a complex of a therapeutic agent and a carrier. Individual drug-loaded microspheres of the plurality of microspheres 30 may include one therapeutic agent or a plurality of therapeutic agents. Collectively, the microspheres of the plurality of microspheres 30 may include some drug-loaded microspheres loaded with one specific therapeutic agent or a combination of specific therapeutic agents and other microspheres loaded with a different specific therapeutic agent or combination of specific therapeutic agents.

In some embodiments, the therapeutic agent may be a hydrophilic therapeutic agent, a water-soluble therapeutic agent, or a therapeutic agent that has at least some solubility in an aqueous solution. In some embodiments, the therapeutic agent may be a chemotherapeutic agent having at least some efficacy for treating a disease such as cancer. In some embodiments, the therapeutic agent may be a chemotherapeutic agent having at least some efficacy for treating a cancer such as hepatocellular carcinoma, liver cancer, prostate cancer, or breast cancer. The therapeutic agent may have one or more chemical moieties or atomic centers having a positive or negative charge or affinity. Examples of specific therapeutic agents may include, without limitation, doxorubicin, sorafenib, vandetanib, nivolumab, ipilimumab, regorafenib, irinotecan, epirubicin, pirarubicin, 5-fluorouracil, cisplatin, floxuridine, mitomycin C, derivatives of any of the foregoing, prodrugs of any of the foregoing, therapeutically acceptable salts or crystalline forms of any of the foregoing, or combinations of any of the foregoing. Further examples of suitable therapeutic agents include, without limitation, pirarubicin, mitoxantrone, tepotecan, paclitaxel, carboplatin, pemetrexed, penistatin, pertuzumab, trastuzumab, and docetaxel.

In some embodiments, the therapeutic agent may be a radiotherapeutic agent having at least some efficacy for treating a disease such as cancer. In some embodiments, the therapeutic agent may be a radiotherapeutic agent having at least some efficacy for treating a cancer such as hepatocellular carcinoma, liver cancer, prostate cancer, or breast cancer. The radiotherapeutic agent may include a radioisotope such as a beta-gamma emitter that emits sufficient gamma radiation to enable imaging. Examples of specific radiotherapeutic agents include, without limitation, bismuth-213, boron-10, cesium-131, cesium-137, cobalt-60, dysprosium-165, erbium-169, holmium-166, iodine-125, iodine-131, iridium-192, iron-59, lead-212, lutetium-177, molybdenum-99, palladium-103, phosphorus-32, potassium-42, radium-223, rhenium-186, rhenium-188, samarium-153, selenium-75, sodium-24, strontium-89, technetium-99m, thorium-227, xenon-133, ytterbium-169, ytterbium-177, and yttrium-90. Some other examples include actinium-225, astatine-211, bismuth-213, carbon-11, nitrogen-13, oxygen-15, fluorine-18, cobalt-57, copper-64, copper-67, fluorine-18, gallium-67, gallium-68, germanium-68, indium-111, iodine-123, iodine-124, krypton-81m, rubidium-82, strontium-82, and thallium-201. In some specific embodiments, the plurality of microspheres 30 may include drug-loaded microspheres comprising yttrium-90.

In some embodiments, the water-swellable polymer material or some portion thereof generally surrounds the therapeutic agent or the complex including the therapeutic agent. In some embodiments, a water-soluble polymer material shell may encapsulate a core that holds the therapeutic agent or complex. In other embodiments, the therapeutic agent or the complex may be physically disposed within a matrix, network, or pore structure of a water-swellable polymer material that may or may not have a core within an outer shell.

In some embodiments, the therapeutic agent of the drug-loaded microbead may generally surround the microspheres of the microbead material but lack of covalent chemical bonds between the therapeutic agent and the microbead material. Despite lacking covalent chemical bonds, the therapeutic agent and microbead material may have noncovalent intermolecular interactions such as ionic interactions or a van der Waals interaction. In some embodiments, the therapeutic agent of the drug-loaded microbead may generally surround the microbead material and lack covalent chemical bonds to the polymer backbone water-swellable polymer material, yet the therapeutic agent may be chemically bonded to a functional group of the water-swellable polymer material. In some embodiments, the therapeutic agent is not chemically bonded to the water-swellable polymer material at all.

The drug-loaded microspheres may include an amount of therapeutic agent that has a desired therapeutic effect or activity, based on the intended use for the plurality of microspheres 30 and the particular therapeutic agent present in the individual microspheres. The amount of therapeutic agent in the individual drug-loaded microspheres of the plurality of microspheres 30 may be adjusted through particular techniques involved during drug loading, such as loading time, loading temperature, or concentration of therapeutic agent in a loading solution, for example. The amount of therapeutic agent in the individual drug-loaded microspheres of the plurality of microspheres 30 may be adjusted through synthetic techniques involved for synthesizing the microspheres themselves, such as through adjusting polymer molecular weights, degree of hydrogel crosslinking, polymer density, or polymer porosity of the water-swellable polymer material. For example, when doxorubicin is the therapeutic agent, the amount of drug loading in the drug-loaded microspheres may be adjusted with respect to the number of negative charges in the polymer backbone of the water-swellable polymer material. Similarly, when sorafenib is the therapeutic agent, the sorafenib may be embedded within polymeric micelles or liposomes that may be embedded within the microbead structure. In some embodiments, the amount of therapeutic agent in the individual microspheres of the drug-loaded microspheres may be adjusted through choice of the carrier.

In some embodiments, when the therapeutic agent is a radiotherapeutic agent, the radiotherapeutic agent may be loaded into the microspheres by a precipitation method. For example, when yttrium-90 is the therapeutic agent, such precipitation methods may include preparing a solution of soluble yttrium salt (e.g., $YCl_3$) for which at least a portion of the yttrium is yttrium-90, chemically converting the soluble salt to small precipitates of an insoluble salt such as yttrium phosphate ($YPO_4$), adding microspheres to solution containing the precipitates, and causing the yttrium phosphate to nucleate onto the surfaces of the beads and, if the microbead is porous, into at least some of the pores. In another example, such precipitation methods may include adding microspheres to a solution of soluble yttrium (e.g., $YCl_3$) for which at least a portion of the yttrium is yttrium-90, allowing the soluble yttrium to penetrate into the pores of the microspheres, and then converting the soluble yttrium to insoluble yttrium, which may include yttrium phosphate ($YPO_4$), yttrium sulfate ($Y_2(SO_4)_3$), and yttrium carbonate ($Y_2(CO_3)_3$). In another example, yttrium-90 may be bonded to or coated onto surfaces of the microbead.

In example embodiments, the individual microspheres of the plurality of microspheres 30 may include from about 1% by weight to about 25% by weight, or from about 1% by weight to about 20% by weight, or from about 1% by weight to about 15% by weight, or from about 2% by weight to about 25% by weight, or from about 5% by weight to about 25% by weight, or from about 10% by weight to about 25% by weight therapeutic agent, based on the total weight of the individual microspheres in the plurality of microspheres 30.

In some embodiments, the drug-loaded microbead may include a complex of a carrier and a therapeutic agent. In the complex, the therapeutic agent may be chemically bonded to the carrier or may be associated with the carrier by a non-covalent means such as encapsulation or a van der Waals interaction. In embodiments, the complex may be embedded within the microbead material. In further embodiments, the complex may be embedded within the water-swellable polymer material. When the complex is embedded within the microbead material, the carrier may be chemically bonded to the microbead material while the therapeutic agent is not chemically bonded to the microbead material. Without intent to be bound by theory, it is believed that when the therapeutic agent is bonded or associated with the carrier but is not chemically bonded to the microbead material, the drug-loaded microspheres of the plurality of microspheres 30 may be less susceptible to shrinking as a result of replacing water molecules with drug molecules during drug loading. Accordingly, the final size distribution of the drug-loaded microspheres may be controlled more readily by selecting appropriate microbead sizes before the therapeutic agent is loaded.

In embodiments in which the drug-loaded microbead includes a complex of the carrier and the therapeutic agent, the carrier may be any pharmaceutically-acceptable compound that can complex with or encapsulate the therapeutic agent. In some embodiments, the carrier may have charged chemical groups or chemical groups with dipole moments that interact with corresponding chemical groups of the therapeutic agent having an opposite charge or opposite dipole moment. If the carrier is a polymeric material, the carrier may be a different material from the water-swellable polymer material. Non-limiting examples of suitable carriers include polysaccharides, liposomes, polymeric micelles, Pluronics, polycaprolactone-b-methoxy-PEG, poly(aspartic acid)-b-PEG, poly(benzyl-L-glutamate)-b-PEG, poly(D,L-lactide)-b-methoxy-PEG, poly($\beta$-benzyl-L-asparate)-b-PEG). Non-limiting examples of polysaccharides include dextrans and dextran sulfates such as dextran sodium sulfate. In one example embodiment, the carrier may include a dextran sodium sulfate having a weight-average molecular weight of from about 40 kDa (kilodalton) to about 500 kDa, or from about 50 kDa to about 300 kDa, or from about 100 kDa to about 300 kDa, or about 100 kDa to about 200 kDa.

In example embodiments, the individual microspheres of the plurality of microspheres 30 may include from about 1% by weight to about 40% by weight, or from about 1% by weight to about 30% by weight, or from about 1% by weight to about 25% by weight, or from about 1% by weight to about 20% by weight, or from about 5% by weight to about 40% by weight, or from about 10% by weight to about 40% by weight, or from about 20% by weight to about 40% by weight carrier, based on the total weight of the individual microbead in the plurality of microspheres 30.

In example embodiments, the individual microspheres of the plurality of microspheres 30 include water. In example embodiments, the individual microspheres of the plurality of microspheres 30 according to embodiments may have a low water content such as less than 1% by weight, or less than 0.5% by weight, or less than 0.1% by weight, or less than 0.05% (500 ppm) by weight, or less than 0.02% (200 ppm) by weight, or less than 0.01% (100 ppm) by weight, or less than 0.005 (50 ppm) by weight, or less than 0.002% (20 ppm) by weight, or less than 0.001% (10 ppm) by weight water, based on the total weight of the individual microspheres. Without intent to be bound by theory, it is believed that a low water content of the microbead increases the shelf-life and long-term stability of the microbead. Further, it is believed that water contents significantly greater than 1% by weight (such as 2%, 3%, 5%, or 10%, for example) based on the total weight of the microbead, may lead to decomposition or hydrolysis of the therapeutic agent, instability or breaking apart of the water-swellable polymer, or a combination of these, within a few days or even a few hours, such that the microbead cannot be used for embolization procedures, even if the microbead is rehydrated. It is believed that the shelf-life and long-term stability of having water contents significantly greater than 1% by weight are not sufficiently long to ensure viability of the therapeutic agent over the time period from manufacture of the microbead to use of the in an embolization procedure. It is believed that selection of the water-swellable polymer material may correlate with the ability for water to be removed from the microspheres by lyophilization or other drying technique or combination of drying techniques in an amount sufficient to prevent decomposition of the therapeutic agent.

A low water content of the microbead, as previously described, may be attained by drying techniques. In this regard, the microspheres may be dry or nearly dehydrated compositions of the microspheres containing the embedded therapeutic agent or the embedded complex of the therapeutic agent and the carrier. The microspheres may have a powder-like consistency. Accordingly, the microspheres may be made suitable for injection into a subject being treated by rehydrating the microspheres so that the plurality of microspheres 30 may be suitable for embolization. Regardless, the microspheres may be provided in such a form that a physician needs to add only an aqueous solution such as water or physiologically buffered saline solution to the plurality of microspheres 30 to prepare the plurality of microspheres 30 for use in an embolization procedure.

Reference will now be made in detail to embodiments of methods of containing radioactive microspheres. In embodiments, the method of containing radioactive microspheres may include storing a plurality of microspheres comprising a diamagnetic material in a container comprising one or more magnetic fields and whereby the plurality of microspheres contained in the container interact with the one or more magnetic fields of the container 10 in a manner that prevents direct contact of the plurality of microspheres to the container. Storing the plurality of microspheres 30 in the container 10 may further include loading the plurality of microspheres 30 into the container 10 per any suitable manufacturing or shipping process. In some embodiments, the method may further include activating one or more magnetic components of the container 10, as previously described. In embodiments, activating the one or more magnetic components may include applying an electric current to the container. In embodiments, the magnetic components may be selectively activated by an electronic interaction, such as by a battery and a switch or other suitable activating means. The diamagnetic levitation between the plurality of microspheres 30 and the container 10 may keep the spheres from settling in the container 10 or coming into direct contact with the walls of the container 10.

The present disclosure includes one or more non-limiting aspects. A first aspect may include a microsphere containment system for storing microspheres including a diamagnetic material, the system comprising: a microsphere container comprising walls that define a containment space in the microsphere container, the walls comprising at least one magnetic component configured to produce a magnetic field within the containment space; wherein microspheres including a diamagnetic material, when stored within the containment space, interact with the magnetic field within the containment space in a manner that prevents direct contact of the microspheres with the walls of the microsphere container.

A second aspect may include the first aspect, wherein the magnetic component is chosen from permanent magnets, ferromagnetic elements, electromagnets, or combinations thereof.

A third aspect may include any preceding aspect, wherein the magnetic field within the containment space comprises multiple zones having varying magnitudes of magnetic field strength.

A fourth aspect may include any preceding aspect, further comprising microspheres stored within the containment space, the microspheres comprising a diamagnetic material.

A fifth aspect may include the fourth aspect, wherein the diamagnetic material comprises carbon, a diamagnetic metal, or combination thereof.

A sixth aspect may include any of the fourth through fifth aspects, wherein at least a portion of the microspheres have a core-shell morphology.

A seventh aspect may include the sixth aspect, wherein the diamagnetic material is the core of the core-shell morphology.

An eighth aspect may include any of the fourth through seventh aspects, wherein the microspheres further comprise a chemotherapeutic material, a radiotherapeutic material, or both.

A ninth aspect may include any of the fourth through eighth aspects wherein the microspheres comprises yttrium 90.

A tenth aspect may include any of the fourth through ninth aspects, wherein the microsphere container is a syringe barrel.

An eleventh aspect may include a method of containing radioactive microspheres, the method comprising: loading microspheres comprising a diamagnetic material into a microsphere container comprising walls that define a containment space in the microsphere container, the walls comprising at least one magnetic component configured to produce a magnetic field within the containment space; and whereby the microspheres in the microsphere container interact with the magnetic field in a manner that prevents direct contact of the microspheres to the container.

A twelfth aspect may include the eleventh aspect, wherein the diamagnetic material comprises carbon, and a diamagnetic metal, or both.

A thirteenth aspect may include the eleventh through twelfth aspects, wherein at least a portion of the microspheres have a core-shell morphology.

A fourteenth aspect may include the eleventh through thirteenth aspects, wherein the diamagnetic material is the core of the core-shell morphology.

A fifteenth aspect may include the fourteenth aspect, wherein the one or more magnetic components are chosen from permanent magnets, ferromagnetic elements, electromagnets, or combinations.

A sixteenth aspect may include the thirteenth aspect, wherein the magnetic field within the containment space comprise multiple zones having varying magnitudes of magnetic field strength.

A seventeenth aspect may include the eleventh through sixteenth aspects, wherein the magnetic component comprises an electromagnet, the method further comprising applying an electric current to the electromagnet to produce the magnetic field.

An eighteenth aspect may include the eleventh through seventeenth aspects, wherein the microspheres further comprise a chemotherapeutic material, a radiotherapeutic material, or both.

A nineteenth aspect may include the eleventh through eighteenth aspects, wherein the microspheres comprise yttrium 90.

A twentieth aspect may include the eleventh through nineteenth aspects, wherein the microsphere container is a syringe barrel.

For the purposes of describing and defining the present disclosure, it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications might be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A microsphere containment system for storing microspheres including a diamagnetic material, the system comprising:
   a microsphere container comprising walls that define a containment space in the microsphere container, the walls comprising at least one magnetic component configured to produce a magnetic field within the containment space;
   further comprising microspheres stored within the containment space, the microspheres comprising a diamagnetic material, wherein the microspheres including the diamagnetic material, when stored within the containment space, interact with the magnetic field within the containment space in a manner that prevents direct contact of the microspheres with the walls of the microsphere container, wherein the microspheres further comprise a chemotherapeutic material, a radiotherapeutic material, or both.

2. The system of claim 1, wherein the magnetic component is chosen from permanent magnets, ferromagnetic elements, electromagnets, or combinations thereof.

3. The system of claim 1, wherein the magnetic field within the containment space comprises multiple zones having varying magnitudes of magnetic field strength.

4. The system of claim 1, wherein the diamagnetic material comprises carbon, a diamagnetic metal, or combination thereof.

5. The system of claim 1, wherein at least a portion of the microspheres have a core-shell morphology.

6. The system of claim 5, wherein the diamagnetic material is the core of the core-shell morphology.

7. The system of claim 1, wherein the microspheres comprises yttrium-90.

8. The system of claim 1, wherein the microsphere container is a syringe barrel.

9. A method of containing radioactive microspheres, the method comprising:
loading microspheres comprising a diamagnetic material into a microsphere container comprising walls that define a containment space in the microsphere container, the walls comprising at least one magnetic component configured to produce a magnetic field within the containment space; and
whereby the microspheres in the microsphere container interact with the magnetic field in a manner that inhibits direct contact of the microspheres to the microsphere container, wherein the microspheres further comprise a chemotherapeutic material, a radiotherapeutic material, or both.

10. The method of claim 9, wherein the diamagnetic material comprises carbon, and a diamagnetic metal, or both.

11. The method of any claim 9, wherein at least a portion of the microspheres have a core-shell morphology.

12. The method of claim 11, wherein the diamagnetic material is the core of the core-shell morphology.

13. The method of claim 12, wherein the at least one magnetic component is chosen from permanent magnets, ferromagnetic elements, electromagnets, or combinations.

14. The method of claim 11, wherein the magnetic field within the containment space comprise multiple zones having varying magnitudes of magnetic field strength.

15. The method of claim 9, wherein the magnetic component comprises an electromagnet, the method further comprising applying an electric current to the electromagnet to produce the magnetic field.

16. The method of claim 9, wherein the microspheres comprise yttrium-90.

17. The method of claim 9, wherein the microsphere container is a syringe barrel.

* * * * *

UNITED STATES PATENT AND TRADEMARK OFFICE
CERTIFICATE OF CORRECTION

| | | |
|---|---|---|
| PATENT NO. | : 12,131,832 B2 | Page 1 of 1 |
| APPLICATION NO. | : 17/055727 | |
| DATED | : October 29, 2024 | |
| INVENTOR(S) | : Casey Tyler Hebert | |

It is certified that error appears in the above-identified patent and that said Letters Patent is hereby corrected as shown below:

In the Claims

In Column 20, Line(s) 1, Claim 11, before "claim 9", delete "any".

Signed and Sealed this
Fifteenth Day of April, 2025

Coke Morgan Stewart
*Acting Director of the United States Patent and Trademark Office*